(12) United States Patent
Balakrishnan et al.

(10) Patent No.: US 12,009,084 B2
(45) Date of Patent: Jun. 11, 2024

(54) APPAREL AND LOCATION INFORMATION SYSTEM

(71) Applicant: NIKE, Inc., Beaverton, OR (US)

(72) Inventors: SantoshKumar Balakrishnan, Portland, OR (US); Jordan M. Rice, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/943,455

(22) Filed: Sep. 13, 2022

(65) Prior Publication Data

US 2023/0005591 A1  Jan. 5, 2023

Related U.S. Application Data

(63) Continuation of application No. 16/401,855, filed on May 2, 2019, now Pat. No. 11,468,976, which is a
(Continued)

(51) Int. Cl.
*G16H 20/30* (2018.01)
*A61B 5/11* (2006.01)
(Continued)

(52) U.S. Cl.
CPC ............ *G16H 20/30* (2018.01); *G16H 15/00* (2018.01); *G16H 20/40* (2018.01); *G16Z 99/00* (2019.02); *A61B 5/002* (2013.01); *A61B 5/11* (2013.01); *G09B 19/0038* (2013.01); *G16H 40/67* (2018.01)

(58) Field of Classification Search
None
See application file for complete search history.

(56) References Cited

U.S. PATENT DOCUMENTS 5,692,324 A * 12/1997 Goldston ............. A43B 1/0036
36/137
6,050,962 A * 4/2000 Kramer .................. G06F 3/011
600/595
(Continued)

FOREIGN PATENT DOCUMENTS

CN   1998047 A   7/2007
CN   101193566 A  6/2008
(Continued)

OTHER PUBLICATIONS

Oct. 14, 2014—(WO) ISR and WO—App. No. PCT/US2014/022616.
(Continued)

*Primary Examiner* — Mohammad Ali
*Assistant Examiner* — Kelvin Booker
(74) *Attorney, Agent, or Firm* — Banner & Witcoff, Ltd.

(57) ABSTRACT

Systems and methods are provided for calculating athletic activity parameters. Multiple housings are position at different locations on a user's body. The housings are configured to be removably engaged with an electronic module that includes a sensor and a processor configured to calculate athletic activity parameters. Each housing is connected to or includes an identification memory that stores information identifying a location of the housing. The electronic module uses the location information to select an algorithm to use when calculating the athletic activity parameters.

18 Claims, 9 Drawing Sheets

Related U.S. Application Data continuation of application No. 13/826,123, filed on Mar. 14, 2013, now Pat. No. 10,318,708.

(51) Int. Cl.

| | | |
|---|---|---|
| *G09B 19/00* | (2006.01) | |
| *G16H 15/00* | (2018.01) | |
| *G16H 20/40* | (2018.01) | |
| *G16H 40/67* | (2018.01) | |
| *G16Z 99/00* | (2019.01) | |
| *A61B 5/00* | (2006.01) | |

(56) References Cited

U.S. PATENT DOCUMENTS

| | | | |
|---|---|---|---|
| 6,484,419 B1 | 11/2002 | Rohde et al. | |
| 7,171,331 B2 | 1/2007 | Vock et al. | |
| 7,584,016 B2 | 9/2009 | Weaver | |
| 7,602,301 B1* | 10/2009 | Stirling | A61B 5/22 340/573.7 |
| 7,607,243 B2 | 10/2009 | Berner, Jr. et al. | |
| 7,927,253 B2 | 4/2011 | Vincent et al. | |
| 7,953,549 B2 | 5/2011 | Graham et al. | |
| 8,360,904 B2* | 1/2013 | Oleson | A61B 5/1118 482/8 |
| 8,652,009 B2 | 2/2014 | Ellis et al. | |
| 8,740,751 B2 | 6/2014 | Shum | |
| 8,909,543 B2 | 12/2014 | Tropper et al. | |
| 9,265,310 B2 | 2/2016 | Lam | |
| 9,282,893 B2 | 3/2016 | Longinotti-Buitoni et al. | |
| 9,314,665 B2 | 4/2016 | Weast et al. | |
| 9,462,839 B1* | 10/2016 | Eppler, Jr. | G08B 21/182 |
| 9,529,966 B2* | 12/2016 | Weast | G16B 5/00 |
| 9,737,261 B2* | 8/2017 | Coza | G16H 40/67 |
| 9,747,411 B2* | 8/2017 | Weast | G16B 99/00 |
| 9,913,611 B2* | 3/2018 | Wiebe | A61B 5/6804 |
| 9,996,660 B2* | 6/2018 | Weast | G09B 19/0038 |
| 10,019,881 B2* | 7/2018 | Chung | G08B 25/016 |
| 10,369,412 B2* | 8/2019 | Aragones | A61B 5/1121 |
| 10,568,381 B2 | 2/2020 | Walker | |
| 10,734,094 B2* | 8/2020 | Weast | G09B 19/0038 |
| 10,825,561 B2* | 11/2020 | Aragones | G16H 40/67 |
| 11,081,207 B2* | 8/2021 | Weast | G01C 22/006 |
| 2002/0013717 A1 | 1/2002 | Ando et al. | |
| 2004/0225199 A1 | 11/2004 | Evanyk et al. | |
| 2006/0093998 A1 | 5/2006 | Vertegaal | |
| 2006/0281435 A1 | 12/2006 | Shearer et al. | |
| 2007/0010721 A1 | 1/2007 | Chen et al. | |
| 2007/0021269 A1* | 1/2007 | Shum | A61B 5/0024 482/8 |
| 2007/0032220 A1 | 2/2007 | Feher | |
| 2007/0032246 A1 | 2/2007 | Feher | |
| 2007/0063850 A1 | 3/2007 | Devaul et al. | |
| 2007/0219059 A1 | 9/2007 | Schwartz et al. | |
| 2007/0260421 A1 | 11/2007 | Berner et al. | |
| 2008/0009275 A1 | 1/2008 | Werner et al. | |
| 2008/0096726 A1* | 4/2008 | Riley | A63B 71/0686 482/8 |
| 2008/0125288 A1* | 5/2008 | Case | A43B 3/34 600/300 |
| 2008/0142060 A1 | 6/2008 | Orth et al. | |
| 2009/0093341 A1 | 4/2009 | James et al. | |
| 2009/0102296 A1 | 4/2009 | Greene et al. | |
| 2009/0171163 A1 | 7/2009 | Mates et al. | |
| 2009/0171166 A1 | 7/2009 | Amundson et al. | |
| 2009/0196124 A1 | 8/2009 | Mooring | |
| 2010/0048358 A1 | 2/2010 | Tchao | A63B 24/0084 482/8 |
| 2010/0088023 A1 | 4/2010 | Werner | |
| 2010/0106684 A1 | 4/2010 | Pizzo et al. | |
| 2010/0184563 A1 | 7/2010 | Molyneux et al. | |
| 2010/0184564 A1* | 7/2010 | Molyneux | A43B 5/02 482/1 |
| 2010/0298656 A1 | 11/2010 | McCombie et al. | |
| 2011/0098928 A1 | 4/2011 | Hoffman et al. | |
| 2011/0144573 A1 | 6/2011 | Rofougaran et al. | |
| 2011/0270052 A1 | 11/2011 | Jensen et al. | |
| 2011/0275940 A1 | 11/2011 | Nims et al. | |
| 2011/0304497 A1 | 12/2011 | Molyneux et al. | |
| 2012/0035487 A1 | 2/2012 | Werner et al. | |
| 2012/0041767 A1 | 2/2012 | Hoffman et al. | |
| 2012/0116550 A1* | 5/2012 | Hoffman | A61B 5/6898 700/91 |
| 2012/0183939 A1* | 7/2012 | Aragones | A63B 24/0062 434/247 |
| 2012/0183940 A1* | 7/2012 | Aragones | A61B 5/744 434/247 |
| 2012/0212505 A1* | 8/2012 | Burroughs | H04N 7/183 345/629 |
| 2012/0234111 A1 | 9/2012 | Molyneux et al. | |
| 2012/0251079 A1* | 10/2012 | Meschter | H04N 7/181 386/278 |
| 2012/0268592 A1* | 10/2012 | Aragones | A61B 5/1118 702/19 |
| 2012/0271143 A1* | 10/2012 | Aragones | G09B 5/02 600/595 |
| 2012/0274508 A1 | 11/2012 | Brown et al. | |
| 2012/0277017 A1 | 11/2012 | Boyd et al. | |
| 2012/0277891 A1* | 11/2012 | Aragones | G09B 19/003 700/91 |
| 2012/0283855 A1* | 11/2012 | Hoffman | A63B 24/0021 700/91 |
| 2012/0323496 A1* | 12/2012 | Burroughs | A63B 24/0062 702/41 |
| 2012/0330126 A1 | 12/2012 | Hoppe et al. | |
| 2013/0002533 A1* | 1/2013 | Burroughs | G16H 20/30 345/156 |
| 2013/0019694 A1 | 1/2013 | Molyneux et al. | |
| 2013/0024248 A1* | 1/2013 | Burroughs | G09B 19/0038 705/7.42 |
| 2013/0041590 A1 | 2/2013 | Burich et al. | |
| 2013/0080255 A1* | 3/2013 | Li | G01C 22/006 701/410 |
| 2013/0106603 A1 | 5/2013 | Weast et al. | |
| 2013/0110264 A1 | 5/2013 | Weast et al. | |
| 2013/0171599 A1 | 7/2013 | Bleich et al. | |
| 2013/0211774 A1 | 8/2013 | Bentley et al. | |
| 2013/0245966 A1* | 9/2013 | Burroughs | G16H 20/30 702/44 |
| 2013/0274587 A1 | 10/2013 | Coza et al. | |
| 2013/0274635 A1* | 10/2013 | Coza | G16H 40/63 600/595 |
| 2013/0317367 A1 | 11/2013 | Shuler | |
| 2014/0051946 A1 | 2/2014 | Arne et al. | |
| 2014/0070957 A1* | 3/2014 | Longinotti-Buitoni | A61B 5/02055 340/870.01 |
| 2014/0100678 A1* | 4/2014 | Chapa, Jr. | A63B 71/06 700/92 |
| 2014/0135955 A1* | 5/2014 | Burroughs | A63B 71/0622 700/91 |
| 2014/0156196 A1 | 6/2014 | Martinez et al. | |
| 2014/0206976 A1 | 7/2014 | Thompson et al. | |
| 2014/0228649 A1 | 8/2014 | Rayner et al. | |
| 2014/0244009 A1 | 8/2014 | Mestas | |
| 2014/0278220 A1 | 9/2014 | Yuen | |
| 2014/0318699 A1* | 10/2014 | Longinotti-Buitoni | H05K 1/038 156/247 |
| 2014/0336796 A1* | 11/2014 | Agnew | G09B 5/00 700/91 |
| 2014/0336947 A1 | 11/2014 | Walke et al. | |
| 2014/0342329 A1* | 11/2014 | Debenedetto | G06Q 10/0639 434/247 |
| 2014/0372677 A1* | 12/2014 | Zipperer | G06F 3/0638 711/103 |
| 2015/0044648 A1* | 2/2015 | White | G09B 5/02 434/236 |
| 2015/0057944 A1* | 2/2015 | White | A61B 5/4866 702/19 |
| 2015/0164437 A1 | 6/2015 | McCombie et al. | |

(56) References Cited

U.S. PATENT DOCUMENTS

| | | | |
|---|---|---|---|
| 2015/0177080 A1* | 6/2015 | Esposito | A61B 5/01 73/862.01 |
| 2015/0182795 A1 | 7/2015 | Martikka et al. | |
| 2015/0217163 A1* | 8/2015 | Amis | A63B 24/0062 700/91 |
| 2015/0258413 A1 | 9/2015 | Molyneux et al. | |
| 2015/0262212 A1* | 9/2015 | Schrock | A61B 5/681 705/14.27 |
| 2015/0265903 A1 | 9/2015 | Kolen et al. | |
| 2015/0317801 A1 | 11/2015 | Bentley et al. | |
| 2015/0318015 A1 | 11/2015 | Bose et al. | |
| 2015/0375042 A1 | 12/2015 | Schaffer | |
| 2016/0000374 A1 | 1/2016 | Dandekar et al. | |
| 2016/0022144 A1 | 1/2016 | Hansen | |
| 2016/0038083 A1 | 2/2016 | Ding et al. | |
| 2017/0004358 A1 | 1/2017 | Bose et al. | |
| 2017/0014684 A1* | 1/2017 | Burroughs | A63B 71/0622 |
| 2017/0068778 A1* | 3/2017 | Weast | G16H 20/40 |
| 2017/0086519 A1* | 3/2017 | Vigano' | A63B 71/141 |
| 2017/0164319 A1 | 6/2017 | Skaaksrud et al. | |
| 2017/0196513 A1* | 7/2017 | Longinotti-Buitoni | A61B 5/7405 |
| 2017/0319133 A1* | 11/2017 | Coza | A61B 5/0022 |
| 2017/0329890 A1* | 11/2017 | Weast | G16H 20/30 |
| 2018/0008879 A1* | 1/2018 | Winsper | G16Z 99/00 |
| 2018/0050236 A1* | 2/2018 | Amis | A63B 71/06 |
| 2018/0247706 A1* | 8/2018 | Riley | A61B 5/1118 |
| 2018/0260516 A1* | 9/2018 | Weast | G06F 17/00 |
| 2019/0015745 A1* | 1/2019 | Bentley | A63F 13/46 |
| 2019/0184231 A1* | 6/2019 | Burroughs | G16H 40/63 |
| 2019/0206270 A1* | 7/2019 | Agnew | G06Q 10/101 |
| 2019/0290963 A1* | 9/2019 | Amis | A61B 5/681 |
| 2020/0073630 A1* | 3/2020 | Sayre | G06F 7/00 |
| 2021/0146196 A1* | 5/2021 | Amis | G16H 40/63 |
| 2021/0327556 A1* | 10/2021 | Weast | G06F 17/00 |
| 2022/0262487 A1* | 8/2022 | Aragones | G06V 40/23 |
| 2022/0347523 A1* | 11/2022 | Amis | A63B 71/06 |

FOREIGN PATENT DOCUMENTS

| | | |
|---|---|---|
| CN | 101448417 A | 6/2009 |
| CN | 102341149 A | 2/2012 |
| CN | 102665461 A | 9/2012 |
| CN | 102946748 A | 2/2013 |
| EP | 2025369 A2 | 2/2009 |
| JP | 2008112290 A | 5/2008 |
| JP | 2008546500 A | 12/2008 |
| JP | 2009502325 A | 1/2009 |
| JP | 2009534546 A | 9/2009 |
| JP | 2009535157 A | 10/2009 |
| JP | 2011183173 A | 9/2011 |
| JP | 2011524207 A | 9/2011 |
| JP | 2012055471 A | 3/2012 |
| JP | 2012188799 A | 10/2012 |
| KR | 20120098854 A | 9/2012 |
| WO | 2007001809 A2 | 1/2007 |
| WO | 2007123970 A2 | 11/2007 |

OTHER PUBLICATIONS

Oct. 14, 2014—(EP) Extended Search Report—App. No. 14159818.5.

Chakraborty, S., Wireless Body Area Network in Real-time Monitoring Application, Sep. 11, 2013, University of Cincinnati, Thesis for M.S. in Computer Science.

Chen, M.; Gonzalez, S.; Vasiliakos, A.; Cao, H. and Leung, V.C.M., "Body Area Networks: A Survey", 2011, Mobile Network Applications, vol. 16, pp. 171-193.

Honeine, P.; Mourad, F.; Kallas, M.; Snoussi, H.; Amoud, H. and Francis, C., "Wireless Sensor Networks in Biomedical: Body Area Networks", 2011, 2011 7th International Workshop on Systems, Signal Processing and their Applications.

Javanov, E.; Poon, C.C.Y.; Yang, G.-Z. and Zhang, Y.T., "Guest Editorial Body Sensor Networks: From Theory to Emerging Applications", Nov. 2009, IEEE Transactions on Information Technology in Biomedicine, vol. 13, No. 6.

Barakah, D.M. and Ammad-Uddin, M., "A Survey of Challenges and Applications of Wireless Body Area Network (WBAN) and Role of a Virtual Doctor Server in Existing Architecture", 2012, 3rd Intl. Conf. on Intelligent Systems Modelling and Simulation.

Javanov, Milenkovic, A.; Otto, C. and deGroen, P.C., "A Wireless Body Area Network of Intelligent Motion Sensors for Computer Assisted Physical Rehabilitation", Jan. 28, 2005, Journal of Neuro Engineering and Rehabilitation, 2-6.

T.M. Fernandéz-Caramés and P. Fraga-Lamas, "Towards the Internet of Smart Clothing: A Review on IoT Wearable and Garments for Creating Intelligent Connected E-Textiles," Oct. 1, 2018, Electronics 2018, 7, 405. (Year 2018).

R.D. Hurford, Smart Clothes and Wearable Technology Woodhead Publishing Series in Textiles, 2009, Chapter 2, pp. 25-44 (Year: 2009).

J.J.A. Mendes Jr., M.E.M. Vieira, M.B. Pires and S.L. Stevan Jr., "Sensor Fusion and Smart Sensor in Sports and Biomedical Applications," Jun. 28, 2016, Sensors 2016, 16, 1569 (Year 2016).

C. Torgan, "Kinetics, From Lab Bench to Park Bench," Nov. 6, 2011, Fitness, Health, Science, Sports, Technology. (Year: 2011).

* cited by examiner

APPAREL AND LOCATION INFORMATION SYSTEM

CROSS-REFERENCE TO RELATED APPLICATION

This application is a continuation of U.S. patent application Ser. No. 16/401,855, filed May 2, 2019, which is a continuation of U.S. patent application Ser. No. 13/826,123, filed Mar. 14, 2013, granted as U.S. Pat. No. 10,318,708 on Jun. 11, 2019. The above-referenced applications are entirely incorporated by reference.

FIELD

The present invention relates to systems and methods for monitoring athletic activity and, in particular, to systems and methods that use location or other information when selecting algorithms to use when calculating athletic data.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interests are ignored. This may further decrease a user's interest in participating in athletic activities or using the athletic activity services and systems.

Some systems present audio and/or visual information to users or measure and track performance to encourage individuals to participate in athletic activities. Such systems may use algorithms to track performance data such as speed, acceleration, distance, steps taken, etc. While a lot of research has been performed to develop various algorithms for determining performance data, it can be difficult to select the appropriate algorithm. Some electronic systems are designed to work with a wide range of individuals and utilize generic algorithms that are not as accurate as other algorithms that may be available for specific individuals or specific configurations of systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Exemplary embodiments of the invention include electronic modules that are programmed to calculate athletic activity parameters. A user may have multiple housings that are configured to be removably engaged with the electronic module positioned at various points on his or her body. Each housing may be connected to or include an identification memory that stores information identifying a location of the housing. The electronic module may use the location information to select an algorithm to use when calculating athletic activity parameters with data received from one or more internal or external sensors.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
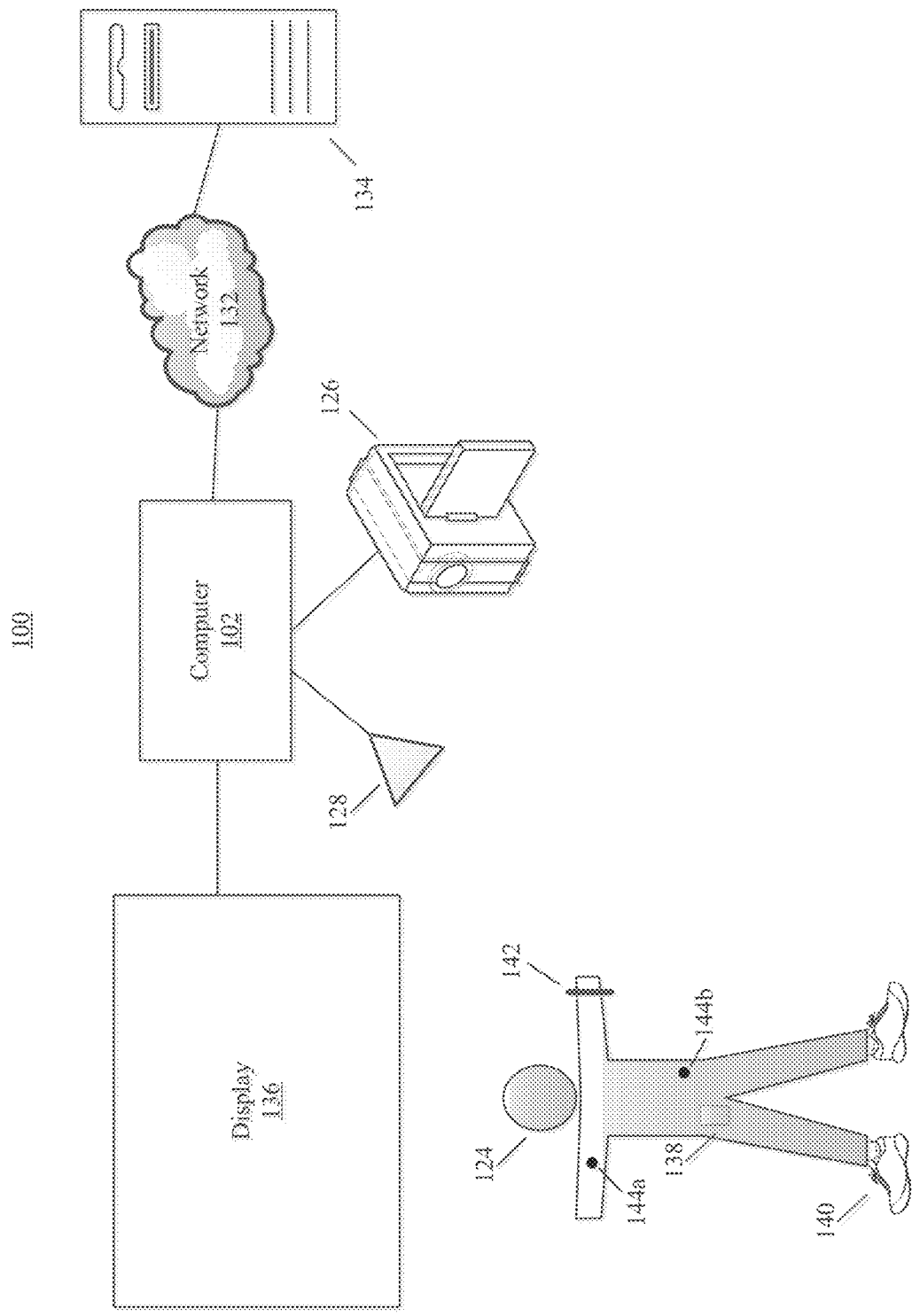

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
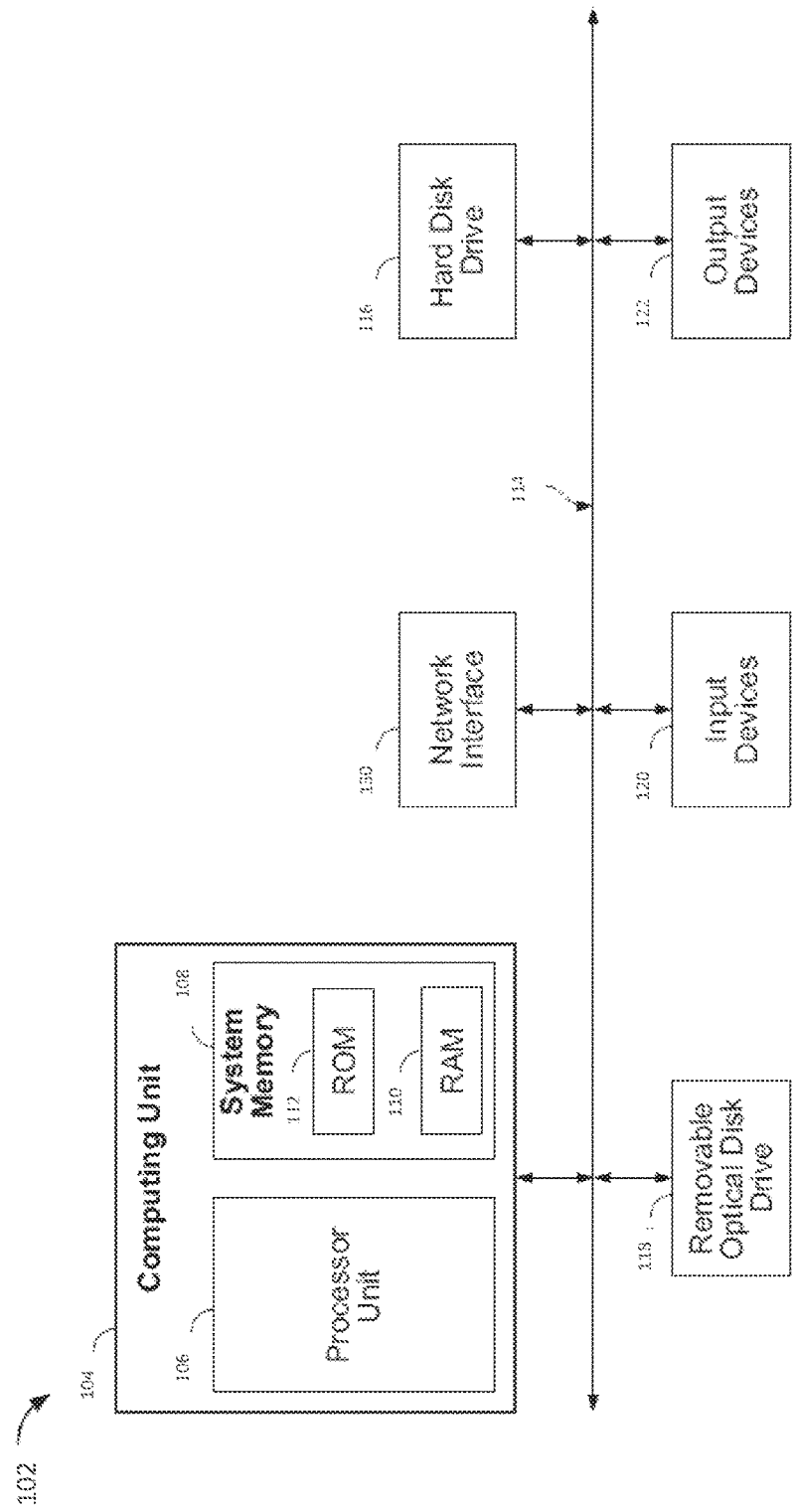

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oregon. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, California or Zune® or Microsoft® Windows devices available from Microsoft of Redmond, Washington. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

ii. Wrist-Worn Device

Figure 2B:
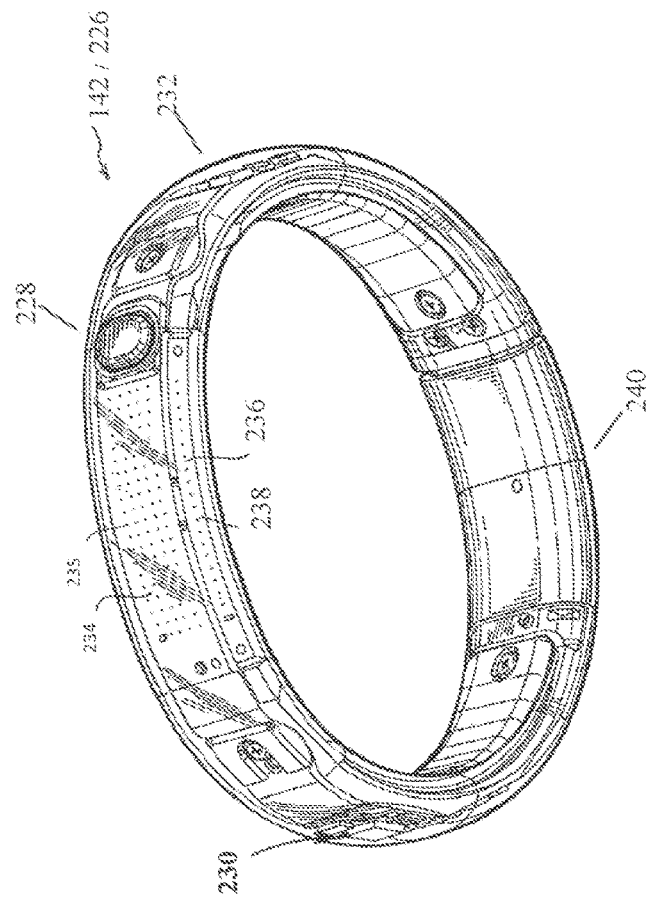
FIGS. 2A-B illustrate example sensor assemblies that may be worn by a user in accordance with example embodiments.
Figure 2A:
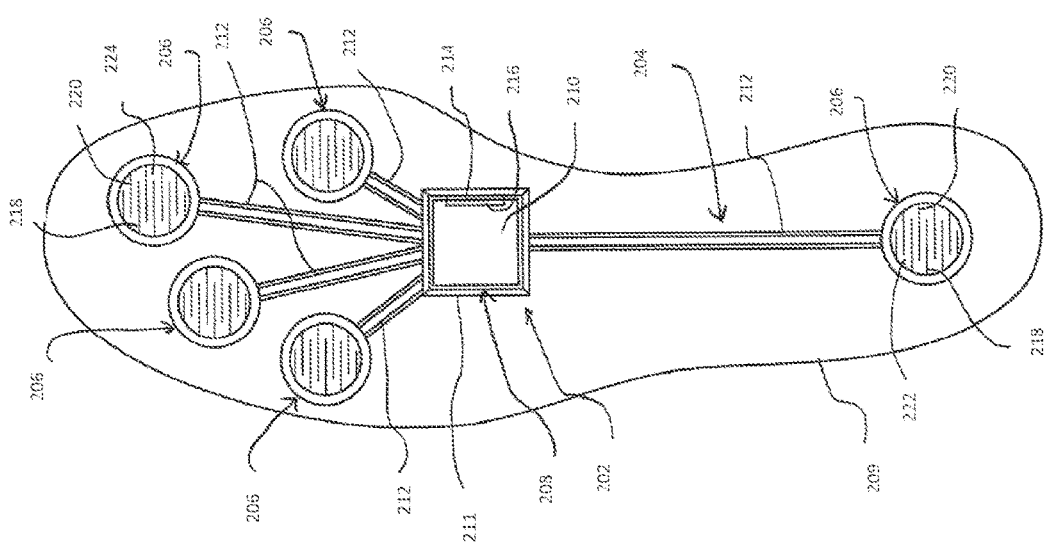

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and energy expenditure such as calories, heart rate, sweat detection, effort, oxygen consumed, and/or oxygen kinetics. Such parameters may also be expressed in terms of activity points or currency earned by the user based on the activity of the user.

II. Energy Expenditure Point Calculations

Figure 3:
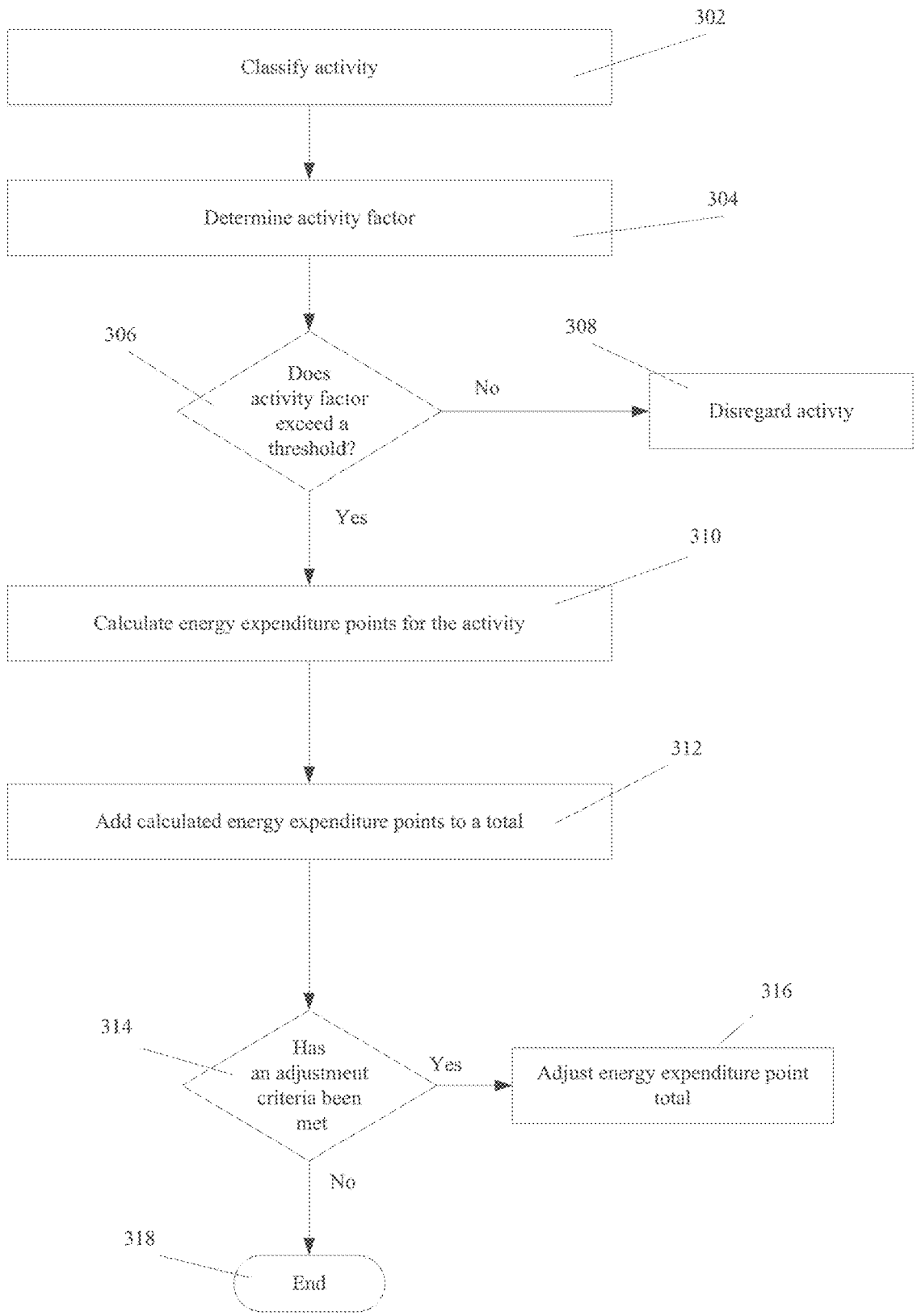
FIG. 3 illustrates a method for calculating energy expenditure, in accordance with an embodiment of the invention.

FIG. 3 illustrates a method for calculating energy expenditure values, such as points, in accordance with an embodiment of the invention. Certain embodiments may classify physical motions of a user. For example, at illustrative step 302, one or more activities may be classified. System 100 may process data received from one or more of the sensors described above to attempt to classify a user's activity. For example, system 100 may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may be created from data obtained from one or more of a plurality of different sensors. For example, a first group of sensors (e.g. sensors 126 and 138) may be utilized in the formation or refinement of a first activity template; however, a second group of sensors (e.g., sensors 128 and 140) may be utilized in the formation or refinement of a second activity template. In yet further embodiments, a third group of sensors, such as sensors 128 and 140 (and/or other sensors), may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 302 may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified. Some embodiments may utilize only templates for running and walking and a best first approach is used to determine whether the user is running or walking.

After at least one of user's 124 activity is classified, step 304 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 302, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

Energy expenditure point calculations me be used in connection with games and competitions. Some games and competitions may limit awarding energy expenditure points for activities that have relatively low activity factors. In some embodiments, awarding energy expenditure points for activities that have relatively low activity factors may also be limited all of the time or in other situations. In step 306 it may be determined whether the activity factor exceeds a threshold value. For example, an exemplary threshold value may be 1.0, 2.0 or 3.0. In another embodiment, the threshold value may equal 2.8. Different games and competitions may use other threshold values. When the activity factor does not exceed the threshold, step 308 may be implemented to disregard the corresponding activity and not use the activity when calculating energy expenditure points.

Another embodiment could have the threshold generally applied, but not when games or competitions are underway, or at least certain games or competitions. The games or competitions may be based on all points. In another embodiment, a threshold may always apply even to games and competitions. In another embodiment, different thresholds may apply by activity, game and/or competition, e.g., one for running briskly, one for running, one for walking, and a default.

In various embodiments of the invention, activity factors are used to calculate energy expenditure points. After at least one of user's 124 activity is classified, in step 310 energy expenditure points may be calculated. The use of energy expenditure points allows for comparison of activity levels and may promote collaboration among users, normalize for competition among users of different capabilities, and otherwise encourage activity. In one embodiment, energy expenditure points are calculated as follows:

$$EEPs = AF * duration \qquad \text{(equation 1)}$$

Wherein:
EEPs=energy expenditure points
AF=activity factor determined in step 304
duration=duration of the activity classified in step 302

Step 310 may be performed at a device that includes sensors that monitor activity and/or at another device that includes a processor, such as a mobile phone (see, e.g., 138) or server (see, e.g., 134). In alternative embodiments equation 1 may be modified to include other factors, a scalar and/or a different combination of terms.

In some embodiments equation 1 may be modified to include a scalar that is multiplied by the activity factor and duration. The scalar may be selected so that typical energy expenditure points fall within a desired range. The range of points may be desired for various games or competitions. The scalar may also represent an intensity of the activity. For example, a first scalar may be correspond to brisk running and a second scalar may correspond to running at a moderate pace. In alternative embodiments additional activity templates and activity factors may be used and may correspond to the various intensities of running or walking.

Variations of equation 1 may be used in other embodiments of the invention. In some embodiments, users may select an equation and/or one or more variables, such as for example, a scalar. Equations may be selected for different games and competitions. In one example a group may set handicaps among the players based on fitness, so that the most fit generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total for their overall energy expenditure. Some point totals may be maintained separate from an overall point total.

Alternative embodiments of the invention may use alternative or additional equations for calculating point values and/or other quantities. The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity points or energy expenditure points and steps. Calculating values that are functions of activity points or energy expenditure points and other variables may be used to compare the efficiencies of various activities. For example, an equation may be used to determine that taking steps at a faster pace may result in activity points or energy expenditure points accumulating at a faster per step pace. Another exemplary equation may determine activity points or energy expenditure points per a predetermined distance or a unit of distance.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity points or energy expenditure points is displayed to a user via display 235 or a display that is part of a mobile device.

After the energy expenditure points are calculated, the calculated points may be combined, such as being added, to a total in step 312. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

Energy expenditure points may be deducted when user 124 has been inactive for a predetermined period of time or enhanced when certain criteria are met. This feature may be included with all calculations or may be used in various games and competitions. For example, in step 314 it may be determined whether an adjustment criteria has been met. The adjustment criteria may include inactivity for a predetermined time period. In some embodiments inactivity is not determined by merely determining that an amount of time has passed since the user was active. Rest, recovery and sleep periods may also be considered. An assessment may require attention not only to inactivity for a predetermined period of time, but also (i) accumulated inactivity over a period of time (particularly in light of the accumulated activity over that time), and/or (ii) the interpositionings of activities and inactivities, e.g. over some previous amount of time before the inactivity period being considered.

In certain embodiments, the quantity may vary for different periods of time. For example, the predetermined quantity of inactivity may be a first value during a period of time in the morning and a second value during a second period of time, such as at night. User 124 may be determined to have been inactive when there is an absence of an activity having a corresponding activity factor that exceeds a threshold. When an adjustment criteria has been met, the total of energy expenditure points may be adjusted in step 316. The adjustment may be a function of duration of inactivity. In some embodiments, a device may warn user 124 (or authorized groups/individuals) that they are close to receiving a reduction in energy expenditure points to encourage activity. It yet other embodiments, an alarm may notify user 124 (and/or other authorized individuals and/or groups) that they have received a reduction of energy expenditure points. In certain embodiments, team-mates and/or competing users may be notified of a reduction (or potential for reduction). In further embodiments, teachers, trainers, and/or parents may more readily monitor the physical activity of others. When a user has not been inactive, the process may end in step 318. Of course, the method shown in FIG. 3 may be repeated at various intervals and allow for tracking points concurrently for different time periods, such as days, weeks and years.

In another aspect, a device, such as device 226, may provide a message based on inactivity or non-active periods. If the device 10 senses that the user has been in a non-active (e.g., low activity) state for a predetermined amount of time, an alert message may be delivered to the indicator system or display to remind the user to become more active. The alert message can be delivered in any of the manners described herein. The threshold levels of a low activity state and amount of inactive time could also vary and be individually set by the user.

In some arrangements, user non-activity or inactivity may also be detected and affect the user's progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like and/or combinations thereof. For arrangements in which a user accumulates activity points to reach an activity point goal, points or a value may be deducted from the user's activity point or other activity metric total when an amount of non-activity (e.g., inactivity or sedentary state) is detected. Various conversion rates for converting inactivity to activity point deductions may be used. In a particular example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

A user's non-active time may include inactive time and sedentary time. Inactivity and sedentary time may be defined by different movement, heart-rate, step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds and/or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations and/or during a specified range of time may be considered detrimental to a user's health. Thus, activity points may be deducted or activity points may be accumulated at a slower rate during these times.

Alternatively or additionally, the amount by which a value of the activity metric (e.g., an activity points) is decreased may be determined based on time of day, location of the user, physical position of the user, level of inactivity and the like. For example, a user may lose greater value in an activity metric and/or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may include placing sensors at different locations of the user's body to detect the individual positions of each body part. The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In the above example, the system may use a portion of the distance such as the vertical distance. By using vertical distance alone or in combination with an absolute distance (e.g., straight line distance between the two sensors), the system may further distinguish between when a user is lying down and standing up. For example, a lying down position may correspond to a very low vertical distance between the knee sensor and chest or waist sensor even though the absolute distance may be larger. A standing position may correspond to a larger vertical distance between the knee sensor and the waist or chest sensor but exhibit a similar absolute distance. In other examples, an angle formed by the various sensors may be used to determine an individual's position. Additionally or alternatively, the location of the user's various body parts may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user by displaying a message or indicator on a device such as the wearable device assembly described herein after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include an non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. The device or system may use the user's profile, or data from various communities, including the data of their friends, in order to suggest activities. The data used to suggest activities may include athletic data and/or non-athletic data. The device or system may also suggest rest or recovery periods, e.g., based upon the user's activity or activities over time or any particular time. When the user has counteracted or accounted for the risks or negative effects of the detected amount of inactivity time, a celebratory message or other indication may be provided.

Warnings, point deductions and/or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like. In a particular example, the user may be required to perform a higher level of activity to halt point deduction.

A device, such as device 226, or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type and/or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data and/or predefined programming and data tables specifying a type and/or duration of activity and a corresponding amount of permissible non-activity.

A device, such as device 226, or other activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location and/or at the same time, the system may recommend that type of activity or workout routine. Other recommendations algorithms and factors may be used.

Activity and inactivity may be tracked across multiple devices, such as the devices shown in FIG. 1A and described above. The devices may include computers, mobile phones, music players, game consoles, set-top boxes, etc. A system that calculates energy expenditure points may link activity and inactivity tracking across multiple devices so that the same activity or inactivity is not counted multiple times. Attaching time stamps to data may facilitate tracking activity and inactivity across multiple devices. In some embodiments, data received from multiple devices is analyzed together to increase the accuracy energy expenditure points.

System 100 may be configured to transmit energy expenditure points to a social networking website. The users may be ranked based on their total number of points for a desired time interval (e.g., rank by day, week, month, year, etc.).

Figure 4:
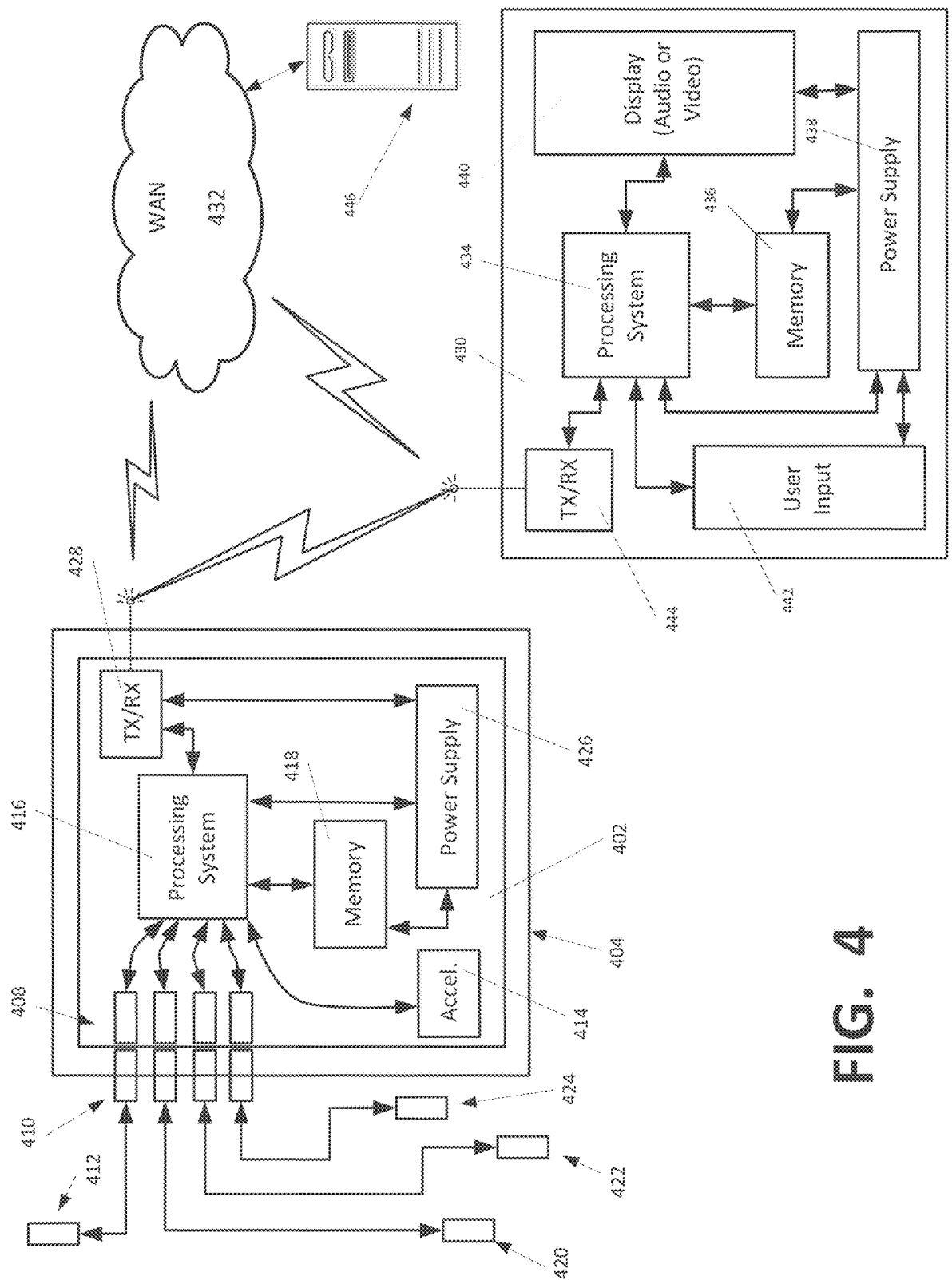
FIG. 4 shows a schematic diagram of an electronic module that may be used to sense and transmit data in accordance with an embodiment of the invention.
Figure 5:
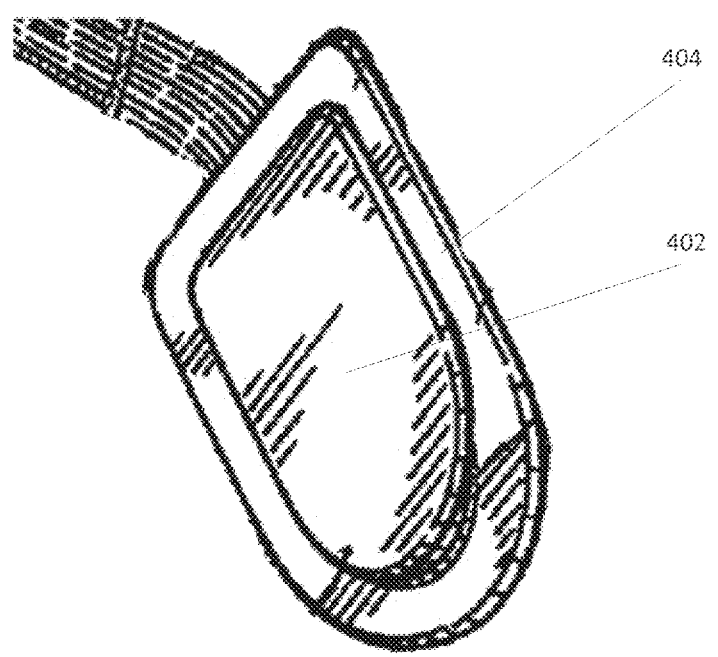
FIG. 5 shows an example configuration in which an electronic module is configured to be removably engaged with a housing in accordance with an embodiment of the invention.
Figure 5:
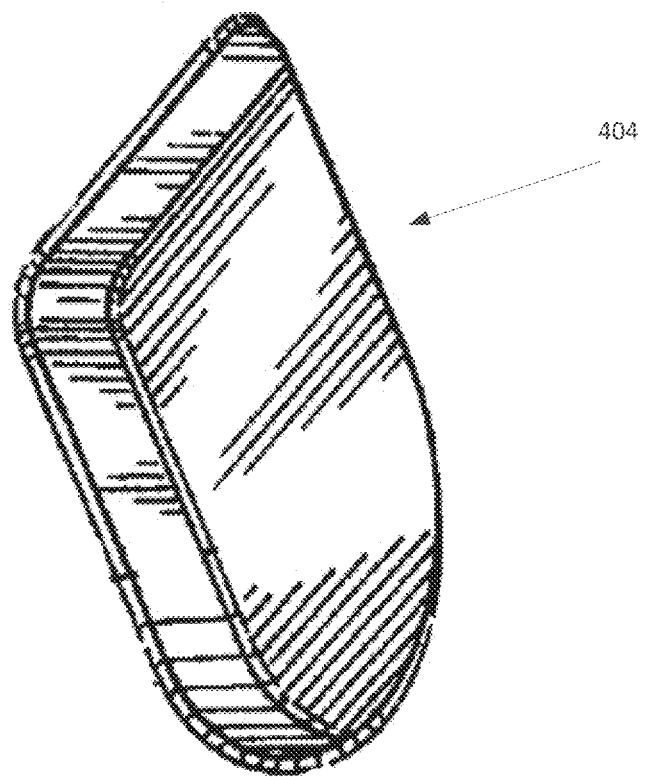

FIG. 4 shows a schematic diagram of an example electronic module 402 that may be used to sense and transmit data in accordance with an embodiment of the invention. Electronic module 402 is configured to be removably engaged with a housing 404. FIG. 5 shows an example configuration in which electronic module 402 is configured to be removably engaged with housing 404. Electronic module 402 may snap into housing 404 or may be held in place with a mechanical structure, magnetic forces, or other mechanisms that allow electronic module 402 to be removably engaged with housing 404.

Housing 404 may be embedded in clothing, footwear, exercise equipment or other devices or locations associated with exercise or activity. Electronic module 402 and housing 404 may each include one or more electrical contacts, such as contacts 408 and 410. An identification memory 412 may be attached to an electrical contact of housing 404 to provide information to electronic module 402 when electronic module 402 is engaged with housing 404. Identification memory 412 may be implemented with a memory that includes a single contact serial interface, such as a 1-Wire® memory, an RFID tag or any other device that stores identifying information. Memory devices that include a single contact serial interface allow for retrieving the contents of the memory with a single contact point. Various embodiments of the invention may utilize active or passive identification memories. Alternative identification memories may use RFID or Near-Field Communication (NFC) components and technologies. Some identification memories may include and/or be connected to one or more associated sensors. Associated sensors may include power sources or receive power from an identification memory. In some embodiments sensors remain in a power off state until receiving a signal from an identification memory or other component.

Identification memory 412 may store information about clothing, location, users, equipment and other types of information used to evaluate athletic activity. Other types of information may include manufacturing data, such as the identification of a manufacturer, manufacturing date, manufacturing time and manufacturing location. Product use information may also be stored in an identification memory.

In one particular embodiment identification memory 412 stores bits of data that identifies a brand and an intended use category. The intended use category may correspond to a sport such as basketball or running. Gender information and information that further identifies apparel, such as a left or right shoe designation and/or a serial number may also be included. Identification memories may be embedded in or associated with apparel during manufacturing. In some embodiments identification memories are activated and/or configured, either at first sale, first use or at some other time after the manufacturing process. Activation and/or configuration may enable operation by providing a connection to a battery or changing a state of an identification memory. Activation and/or configuration information may be provided to a computer device, such as computer device 430 and/or server 446.

Figure 6:
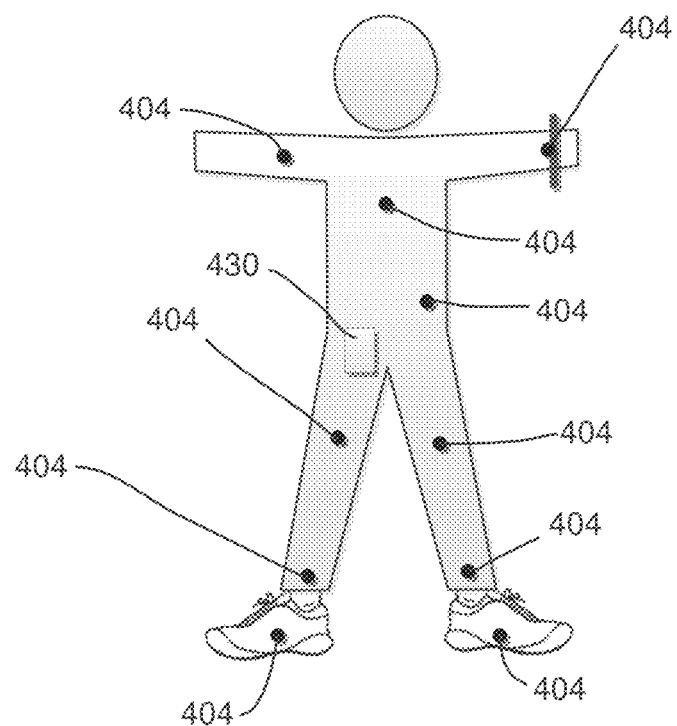
FIG. 6 shows an example of where housing may be attached to or embedded within clothing of a user, in accordance with an embodiment of the invention.

FIG. 6 shows an example of where housing 404 may be attached to or embedded within clothing of a user. The housing may be placed in shirts, shorts, jackets, footwear, wrist worn devices, heart rate monitor straps, and other locations that allow electronic module 402 to determine information, such as activity points. Alternative embodiments of the invention include identification memories embedded in apparel without association with housings. In such embodiments, identification memories may be connected to one or more sensors, actuators, switches, display elements or other electronic component. For example, a shirt sleeve may include an embedded identification memory that stores information relating to the type of shirt and a location of the identification memory. The stored information may be used when selecting or modifying an algorithm. In addition to selecting or modifying an algorithm, an electronic module, such as electronic module 402, may read information from an identification memory and use this information to activate or turn on associated sensors. For example, electronic module 402 may know that a particular identification memory is associated with three sensors and data from one of the sensors will be used by the selected algorithm. In such a case, electronic module 402 may cause the identification memory to activate or turn on the indicated sensor.

Electronic module 402 may include one or more sensors, such as accelerometer 414, and a processing system 416 (e.g., one or more microprocessors) and a memory 418. Memory 418 may store a plurality of algorithms that are used to determine information such as athletic performance parameters and activity points. Algorithms may be optimized to generate results based on the location of electronic module 402. For example, memory 418 may include a plurality of algorithms for determining activity points. In operation, processing system 416 may retrieve information from identification memory 412 that identifies a current location of electronic module 402. The location information may identify apparel such as shirts, pants, shorts, footwear, hats, accessories, etc. Location information may also identify equipment, such as balls, mitts, treadmills, exercise bikes, and other equipment that a user may operate. Location information may further identify a location on apparel, such as in footwear, on a shirt sleeve, etc. With this location information, processing system 416 may retrieve an algorithm that is optimized for determining activity points with accelerometer data when accelerometer 414 is at the indicated location.

Location information may be associated with other information, such as an expected range of motion of apparel. Some apparel is intended to have a loose fit, such as a basketball jersey, while other apparel is intended to have a snug fit, such as an American football jersey. An identification memory may store location and expected range of motion information. Alternatively, an identification memory may store location information and attributes of the apparel and electronic module 402 or some other device may determine an expected range of motion. The resulting information may be used when selecting or modifying an algorithm. Moreover, such information may be used to validate data received from sensors. For example, an identification memory may store information indicating that the location is on a sleeve of a jersey that is intended to be worn snuggly. An accelerometer signal value may be discarded because it exceeds an expected value, while the same value may be valid when it is received from an accelerometer attached to a loose fitting jersey.

Electronic module 402, or some other device may also modify or update one or more algorithms based on information received from one or more identification memories. Modifications may include adding or removing steps, variables, scalars, boundary conditions, parameters, terms and other elements that may be used by algorithms. Modifications may also include setting values for scalars, boundary conditions etc. For example, an identification memory may identify a size of a shoe and the shoe size information may be used to set a value of a scalar in an algorithm. The presence of information stored within an identification memory may also be used to eliminate algorithms from the selection process. For example, information identifying a particular type of footwear may be used to eliminate one or more algorithms.

In addition to modifying one or more algorithms, information received from an identification memory also be used to modify processes implemented with software, firmware, etc. over time. For example, electronic module 402 may use information obtained from an identification memory to both modify an algorithm and alter software that controls the operation of transmission/reception system (TX-RX) 428 to change a frequency of data transmissions. Some information may be used to change a scope of a user's profile data that may be stored in electronic module 402, computer device 430 and/or server 446. In some embodiments identification memories include indicators such as electrochromic displays. A display state may be set as a function of whether the memory has been turned on and/or is providing data that was used to select or modify an algorithm that is currently being used.

In addition to including one or more sensors, electronic module 402 may be connected to one or more external sensors, such as sensors 420, 422 and 424. Sensors 420, 422 and 424 may be accelerometers, pressure sensors, altimeters, gyroscopes or any of the other types of sensors described above. External sensors may include memories that store location information. In some embodiments, the algorithm selected from memory 418 may also be a function of sensor data available, value of the sensor data and external data, such as weather data. For example, sensor 420 may be an accelerometer and processing system 416 select an algorithm from memory 418 that is optimized to be used with data from an external accelerometer and internal accelerometer 414 that is determined to be located within footwear by information stored in identification memory 412. Data from sensor 420 may also be initially analyzed to determine if the user is running or walking and this information may also be used when selecting an algorithm. Some algorithms may not use data from all of the available sensors. Computer device 430 or some other device may be used to inform a user of which sensors are currently being used. In some embodiments, computer device 430, electronic module 402 or some other device may identify available sensors and locations and recommend modifying a location of electronic module 402. For example, electronic module 402 may determine that a user is running, electronic module 402 is attached to a sleeve and based upon the activity and other sensor data available, repositioning electronic module 402 to footwear would produce more accurate results. The repositioning of electronic module 402 may also result in selection of a different algorithm or modification of an algorithm.

Identification memories embedded in apparel may also be used to help identify activities with varying levels of confidence. For example, an identification memory embedded in footwear may include category information that identifies the footwear as intended for use when playing basketball. When this information is received at a mobile phone or other device, the device can assume at a first confidence level that the user is playing basketball. An identification memory embedded in shorts worn by the user may identify the shorts as basketball shorts. When footwear and shorts data is combined with sensor data, the mobile phone or other device may assume at a second confidence level, higher than the first confidence level, that the user is playing basketball. Identification memories may similarly be embedded or attached to equipment to provide similar information. For example, an identification memory may be embedded in a basketball and the information identifying the basketball may be used to identify the activity as basketball at an even higher confidence level. The identification of activities may be used to select and modify algorithms. In some embodiments more general algorithms are selected when activities are identified with relatively lower confidence levels and more accurate algorithms are selected when activities are identified with relatively higher confidence levels. The identification of activities with various confidence levels may also be used to adjust displays and other software, such as the software that controls the operation of transmission/reception system (TX-RX) 428 to change a frequency of data transmissions.

In some embodiments of the invention algorithms may be selected or modified dynamically. Electronic module 402, computer device 430 and/or server 446 may be programmed to periodically select or modify algorithms or select or modify algorithms when conditions change. Conditions may change when different data is received from identification memories. For example, a user may be exercising in a gym and using multiple pieces of equipment at various times. Each piece of equipment may have an identification memory embedded or attached. As the user moves to different equipment and comes within the range of identification memories algorithms may be modified or different algorithms may be selected. Similarly, algorithms may be modified or selected dynamically as the user changes apparel. In some embodiments, error conditions, such as when sensor value or calculated value exceeds a threshold may be used to restart an algorithm selection process.

Electronic module 402 may include additional components, such as a power supply 426 and a transmission/reception system (TX-RX) 428. In one embodiment, power supply 426 may be configured for inductive charging, such as by including a coil or other inductive member. In this configuration, electronic module 402 may be charged by being placed on an inductive pad or other inductive charger. In another embodiment, power supply 426 may additionally or alternately be configured for charging using energy-harvesting technology, and may include a device for energy harvesting, such as a charger that charges through absorption of kinetic energy due to movement of the user. While the example structures of FIG. 4 illustrate the data transmission/reception system (TX-RX) 428 as integrated into the electronic module 402, those skilled in the art will appreciate that a separate component may also be used with embodiments of the invention. Transmission/reception system (TX-RX) 428 may utilize one or more wireless communication channels (including but not limited to: WiFi®, Bluetooth®, Near-Field Communication (NFC), ANT technologies and/or mobile phone technologies).

Electronic module 402 may utilize transmission/reception system (TX-RX) 428 to communicate with a computer device 430 and/or a wide area network 432. Computer device 430 may be an external computer or computer system, mobile phone device, gaming system, or other type of electronic device. The exemplary computer device 430 includes a processing system 434, a memory 436, a power supply 438, a display 440, a user input 442, and a data transmission/reception system 444. Transmission/reception system 444 is configured for communication with electronic module 402 via transmission/reception system 428 of electronic module 402, through any type of known electronic communication, including the contacted and contactless communication methods described above and elsewhere herein. In some embodiments computer device 430 is implemented with a mobile telephone and information from identification memory 412 is transmitted from electronic module 402 to computer device 430. The information from identification memory 412 may be displayed on display 440 or used at processing system 434. Processing system 434 may be programmed to cause display 440 to alert a user when transmission/reception system (TX-RX) 428 is transmitting data and electronic module 402 is not connected to an identification memory, such as identification memory 412. In some embodiments, processing system 416 may be configured to only allow power to be applied to transmission/reception system (TX-RX) 428 when electronic module 402 is connected to an identification memory, such as identification memory 412.

The system shown in FIG. 4 includes a server 446 connected to wide area network 432. Server 446 may compile and allow users to compare performance data. Server 446 may also aggregate information relating to use of products. Electronic module 402 may retrieve identifying information from one or more identification memories and use that information to identify uses of products uses of combinations of products or trends. For example, an identification memory may store product size information and server 446 may aggregate information received from several sources to determine how frequently different sized products are used. Similarly, accessories may also include identification memories that identify accessories and sizes. The obtained product use information may be used when developing future products. For example, the frequency of use of spacers or extension components may be used when determining sizes of similar products in the future. Product size information may also be used with profile data when selecting or modifying an algorithm. For example, a user's profile data may indicate the user's actual wrist size and information included within identification memories of a wrist worn device and a spacer may identify a size of a wrist worn device and a spacer. The resulting information may be used to determine how tightly the wrist worn device is being worn, which may be used to select or modify an algorithm.

Data may also be analyzed at server 446 to recommend products and activities to users. For example, if server 446 determines that a user recently started using a new product, server 446 may recommend activities that use the product. The recommendations may be based on previous activities of the user. The recommendations may be in the form of audio and/or visual data sent to computer device 430. In some embodiments, computer device 430 is implemented with a mobile phone and the recommendation received from server 446 includes an interactive game or a demonstration of how to use the new product. Server 446 or some other computer device may also recommend additional or alternative apparel based upon attributes such as category, color, intended use information received from an identification memory.

Figure 7:
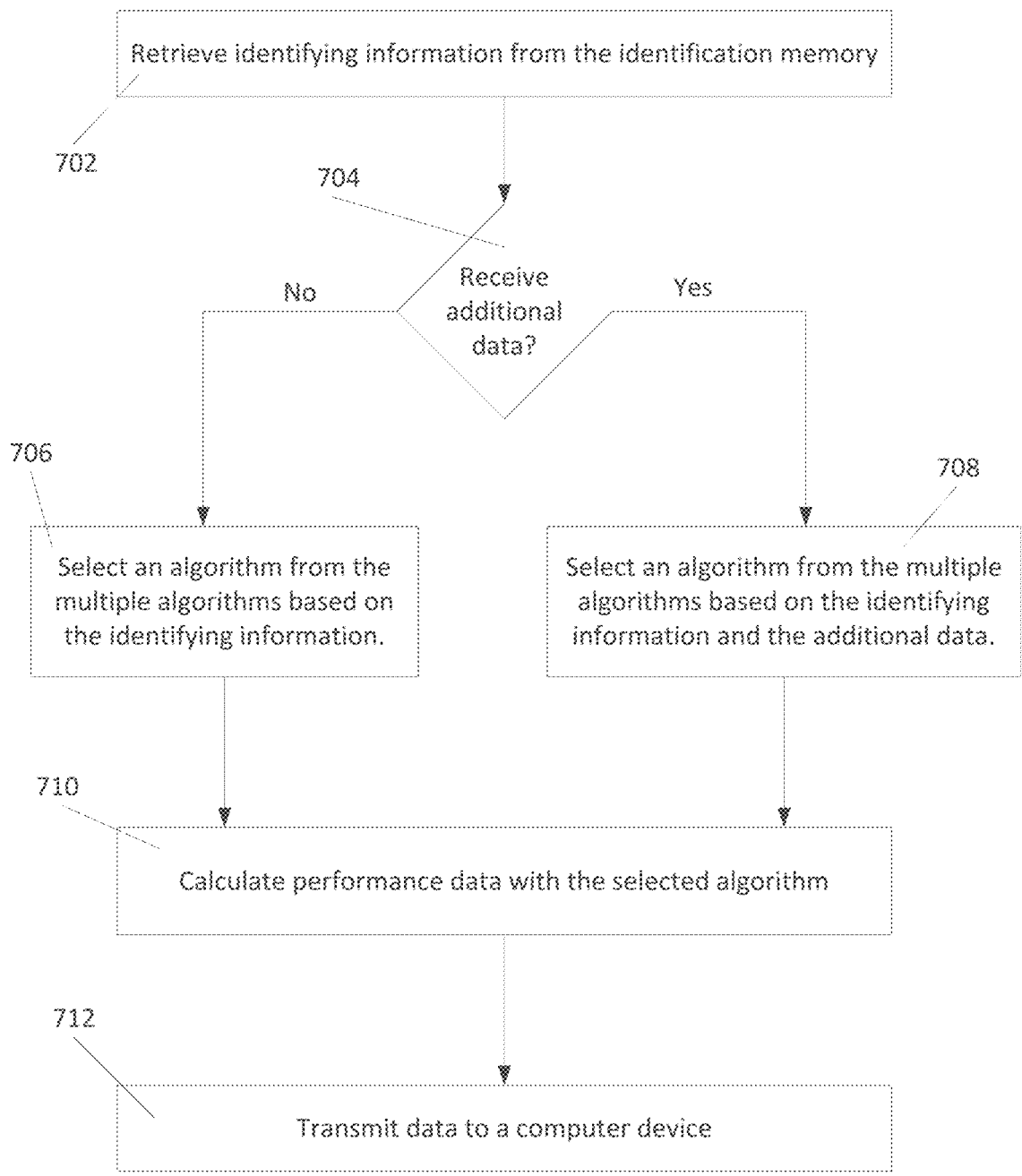
FIG. 7 illustrates a process that may be used to select algorithms and process data in accordance with an embodiment of the invention.

FIG. 7 illustrates a process that may be used by processor or processing systems, such as processing system 416, to select algorithms and process data in accordance with an embodiment of the invention. First, in step 702 identifying information is retrieved from an identification memory. The identifying information may identify equipment and/or a location. The location may correspond to a position on a body of the user. As discussed above, a user may have multiple housings positioned on his or her body and each housing may be attached to or include an identification memory that stores the location information. In step 704 it is determined whether additional data is received. Additional data may include user profile data, data from one or more sensors, environmental data, data relating to the size or configuration of products, data from exercise equipment or any other data that may be used to help select an algorithm to calculate performance data, such as activity points. In some embodiments, data may be received from server 446. The data received from server 446 may include profile data, data relating to past use of a product, past activities and other data that may be used when selecting an appropriate algorithm. Data may also be received from nearby exercise equipment. In one embodiment of the invention, computer device 430 is implemented with a mobile device that includes a camera. The camera may be used to capture bar code or other identifying information from exercise equipment. RFID tags and other devices that store information optically or electrically may also be used to store and provide information to computer device 430 and/or electronic module 402.

When no additional data is received, in step 706 an algorithm is selected based on the identifying information. When additional data is available, an algorithm is selected based on the identifying information and the additional data in step 708. Algorithms may be stored in a memory with metadata that may be used in the selection processes. For example, an algorithm may include metadata that indicates that the algorithm is appropriate to use with female users aged 15-20 years old when an electronic module is located within a right article of footwear and the electronic module receives additional data from a heart rate sensor. Lookup tables and data structures may also be used to associate algorithm properties with algorithms and to facilitate selecting the appropriate algorithm. After an algorithm is selected, in step 710 performance data is calculated with the selected algorithm. Performance data may include speed, acceleration, distance, steps taken, direction, relative movement of certain body portions or objects to others, or other motion parameters which may be expressed as angular rates, rectilinear rates or combinations thereof. Physiological parameters, such as calories, heart rate, sweat detection, effort, oxygen consumed, oxygen kinetics, and other metrics may also be calculated with appropriate algorithms. In some embodiments activity points and activity points earned during predetermined time periods or activity points earned per step or other value are calculated. After the performance data is calculated, the performance data may be transmitted to a computer device in step 712. The transmission may be via a wireless protocol. In some embodiments performance data is received at a server and the server allows multiple users to compare performance data.

Figure 8:
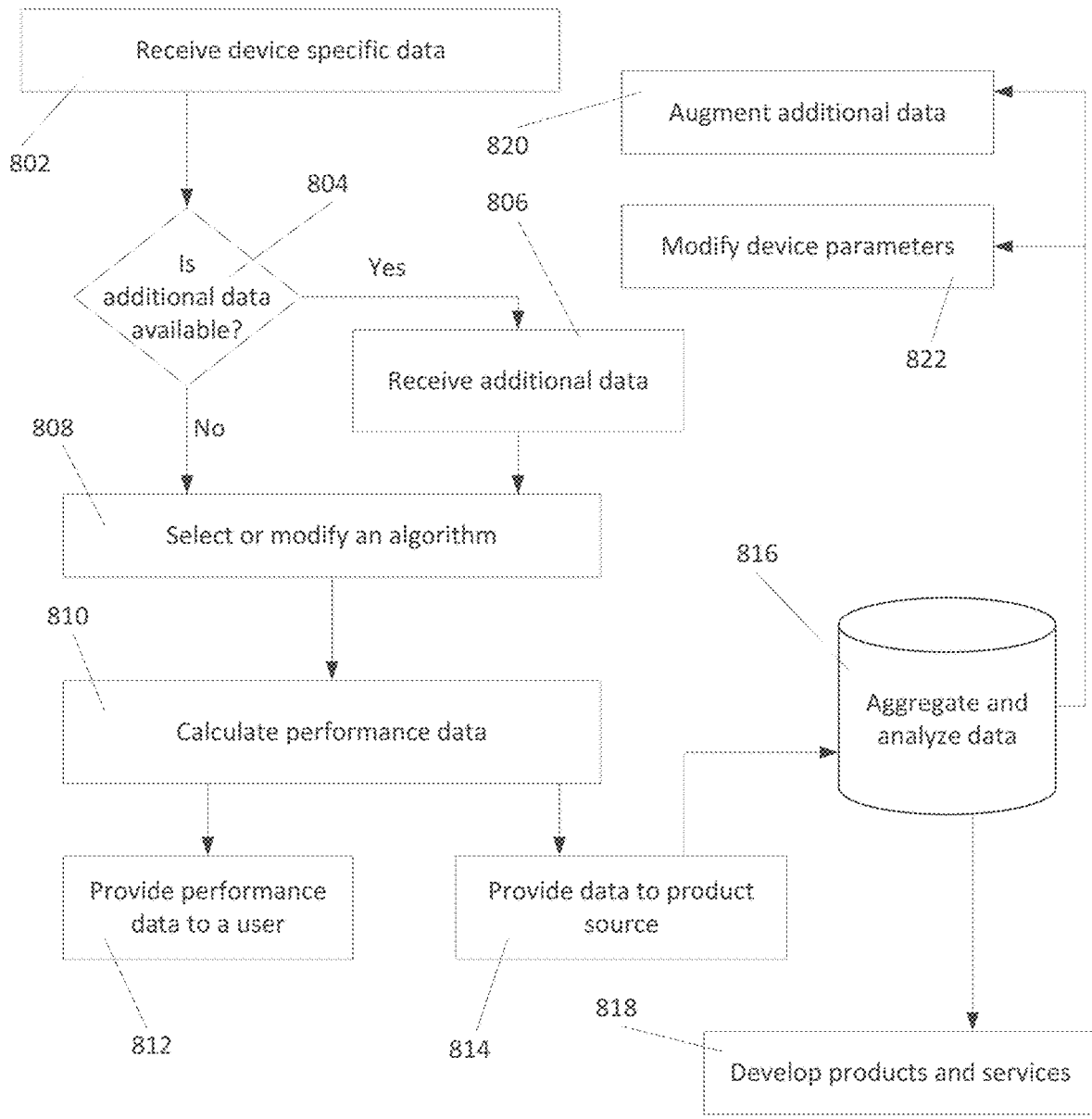
FIG. 8 shows how data may be exchanged in a system and uses of data, in accordance with an embodiment of the invention.

FIG. 8 shows how data may be exchanged in a system, such as the one shown in FIG. 4 and uses of data, in accordance with an embodiment of the invention. First, step 802 device specific data is received. The device specific data may include data from one or more sensors and/or identification memories. The data may be received at a device, such as at electronic module 402, computer device 430 or server 446. Next, in step 804 it is determined whether additional data is available. Additional data may include weather data, use data, profile data or any other data that may be used to help select or modify an algorithm. When additional data is available, the additional data is received in step 806. The additional data may be received at a device, such as at electronic module 402, computer device 430 or server 446. In step 808 an algorithm may be selected or modified. The algorithm may be of the type described above and may be selected or modified as described above. Performance data is next calculated in step 810. Performance data may include speed, acceleration, distance, steps taken, activity points, energy expenditure and other data related to movement and physical fitness.

Performance data may be provided to a user in step 812. Step 812 may include displaying data on computer device 430 or some other device. In step 814 data may be provided to a product source or some other entity such as a manufacturer or third party. The data provided in step 814 may be performance data and/or other data such as product use data, profile data and the additional data received in step 806.

Data may be aggregate and/or analyzed in step 816. Step 816 may include aggregating data received from numerous users and identifying trends and may be performed at a server such as server 446. Step 816 may also include analyzing data from individual users, sensors and equipment. The data aggregated and analyzed in step 816 may be used to develop future products and services in step 818. The same data may be used to modify existing products and services. Aggregated and/or analyzed data may also be used for other purposes, such as augmenting additional data in step 820. The additional data may be received in step 806. Device parameters may also be adjusted in step 822. Device parameters may include settings or adjustments for sensors and/or identification memories.

CONCLUSION

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A computer device configured to be in communication with an identification memory located on a user's body and a sensor connected to the identification memory and configured to monitor activity of a user, the computer device comprising:
   a receiver configured for receiving identifying information from the identification memory and sensor data from the sensor;
   a non-transitory computer-readable medium that contains multiple algorithms for calculating energy expenditure values; and
   a processor programmed with computer-executable instructions that when executed cause the processor to perform the steps comprising:
      receiving the identifying information from the identification memory and the sensor data from the sensor, through the receiver, wherein the identifying information identifies at least one of a location in proximity to the user, a location of the identification memory on the user's body, and an article of athletic equipment to which the identification memory is attached;
      selecting an algorithm from the multiple algorithms based on the identifying information; and
      calculating energy expenditure values from the sensor data using the algorithm.

2. The computer device of claim 1, wherein the energy expenditure values are in the form of activity points.

3. The computer device of claim 1, wherein the computer device is an electronic module configured to be removably engaged with a housing connected on a user's body, wherein the identification memory is attached to the housing.

4. The computer device of claim 1, wherein the computer device is an external device in communication with an electronic module removably engaged with a housing attached to the identification memory and having an interface in communication with the identification memory.

5. The computer device of claim 1, wherein the receiver is further configured for receiving the sensor data from a plurality of sensors configured to monitor the activity of a user.

6. The computer device of claim 1, wherein the processor is further configured for identifying an athletic activity of the user based on the identifying information and the sensor data.

7. The computer device of claim 1, wherein the receiver is further configured for receiving the identifying information from a plurality of different identification memories, and wherein the processor is further configured for selecting the algorithm based on the identifying information from all the identification memories.

8. The computer device of claim 1, wherein the receiver is further configured for receiving additional data from an external device, and wherein the processor is further configured for selecting the algorithm based on the identifying information and the additional data, and wherein the additional data comprises at least one of user profile data, data from one or more additional sensors, environmental data, data relating to size or configuration of products, and data from exercise equipment.

9. A computer device, wherein the computer device is an electronic module configured to be removably engaged with a housing connected on a user's body, comprising:
   a receiver configured for receiving athletic performance data related to a user from an external device associated with the user; and
   a processor programmed with computer-executable instructions that when executed cause the processor to perform the steps comprising:
      receiving the athletic performance data from the external device through the receiver;
      aggregating and analyzing the athletic performance data;
      determining whether additional athletic performance data from a plurality of additional external devices associated with a plurality of different users is available;
      receiving additional athletic performance data from a plurality of additional external devices associated with a plurality of different users, through the receiver;
      aggregating and analyzing the additional athletic performance data along with the athletic performance data; and
      transmitting instructions to modify a parameter of the external device based on the aggregating and analyzing of the athletic performance data and the additional athletic performance data.

10. The computer device of claim 9, wherein the computer-executable instructions, when executed, further cause the processor to perform the steps comprising:
    augmenting additional data based on the aggregating and analyzing of the athletic performance data; and
    transmitting the augmented additional data to the external device.

11. The computer device of claim 10, wherein the additional data comprises at least one of user profile data, data from one or more additional sensors, environmental data, data relating to the size or configuration of products, and data from exercise equipment.

12. A computer device, wherein the computer device is an electronic module configured to be removably engaged with a housing connected on a user's body, comprising:
    a receiver configured for receiving athletic performance data related to a user from an external device associated with the user; and
    a processor programmed with computer-executable instructions that when executed cause the processor to perform the steps comprising:
    receiving the athletic performance data from the external device through the receiver;
    aggregating and analyzing the athletic performance data;
    augmenting additional data based on the aggregating and analyzing of the athletic performance data;
    determining whether additional athletic performance data from a plurality of additional external devices associated with a plurality of different users is available;
    transmitting the augmented additional data to the external device;
    receiving additional athletic performance data from a plurality of additional external devices associated with a plurality of different users, through the receiver;
    aggregating and analyzing the additional athletic performance data along with the athletic performance data; and
    transmitting instructions to modify a parameter of the external device based on the aggregating and analyzing of the athletic performance data and the additional athletic performance data.

13. The computer device of claim 12, wherein the computer-executable instructions, when executed, further cause the processor to perform the step comprising transmitting instructions to modify a parameter of the external device based on the aggregating and analyzing of the athletic performance data.

14. The computer device of claim 12, wherein the additional data comprises user profile data.

15. The computer device of claim 12, wherein the additional data comprises data from one or more sensors.

16. The computer device of claim 12, wherein the additional data comprises environmental data.

17. The computer device of claim 12, wherein the additional data comprises data relating to size or configuration of products.

18. The computer device of claim 12, wherein the additional data comprises data from exercise equipment.

\* \* \* \* \*